United States Patent [19]

Bittner et al.

[11] 4,017,413
[45] Apr. 12, 1977

[54] PROCESS FOR THE PRODUCTION OF SOLUTIONS OR SUSPENSIONS OF CYANURIC CHLORIDE IN AQUEOUS ORGANIC SOLVENTS

[75] Inventors: Friedrich Bittner, Bad Soden, Germany; Heinz Haschke, Weissenstein ob der Drau, Austria; Helmut Suchsland, Rodenbach, Germany; Gerd Schreyer, Hanau, Germany; Werner Schwarze, Frankfurt, Germany

[73] Assignee: Deutsche Gold- und Silber-Scheideanstalt vormals Roessler, Frankfurt, Germany

[22] Filed: Nov. 18, 1975

[21] Appl. No.: 632,952

[30] Foreign Application Priority Data

Nov. 20, 1974 Germany .................... 2454910

[52] U.S. Cl. .................... 252/187 R; 252/182; 252/187 C; 260/248 C; 252/188.3 R
[51] Int. Cl.² .................... B01F 3/08; C07D 251/28
[58] Field of Search .......... 252/182, 187 R, 187 C, 252/188.3 R; 260/248 C; 23/306

[56] References Cited

UNITED STATES PATENTS

| | | | |
|---|---|---|---|
| 3,539,565 | 11/1970 | Evers et al. | 260/248 C |
| 3,575,880 | 4/1971 | Wojahn et al. | 260/248 C |
| 3,741,729 | 6/1973 | Evers et al. | 260/248 C |
| 3,883,515 | 5/1975 | Tandon | 260/249.5 |
| 3,925,377 | 12/1975 | Geiger | 260/248 C |

*Primary Examiner*—Leland A. Sebastian
*Assistant Examiner*—Irwin Gluck
*Attorney, Agent, or Firm*—Cushman, Darby & Cushman

[57] ABSTRACT

There is provided a process for the production of a solution or suspension of cyanuric chloride in a water containing organic solvent wherein the liquid cyanuric chloride and the organic-aqueous solvent are mixed together while being agitated, the liquid cyanuric chloride at a temperature between its melting point and 200° C. is led into the flowing organic-aqueous solvent with a velocity of Vcy (in kg per hour) wherein $$V_{cy} = \frac{P - P_{LM}}{100 - P} \times V_{LM}$$

where
P is the desired concentration of cyanuric chloride in the solution or suspension to be produced in weight %, $P_{LM}$ is the concentration of cyanuric chloride in the solvent used which also includes O, $V_{LM}$ is the velocity of the solvent added in kg/h, and $P_{LM}$, $V_{LM}$ and $T_{LM}$, the temperature of the added solvent, are so selected that the expression $$T_x = \frac{T_{LM} + \frac{V_{cy}}{V_{LM}} \times \frac{C_p(Cy)}{C_p(LM)} \times T_{Cy}}{1 + \frac{V_{cy}}{V_{LM}} \times \frac{C_p(Cy)}{C_p(LM)}}$$

does not exceed the boiling temperature in ° C. of the solvent used and wherein $C_p(LM)$ and $C_p(Cy)$ signify the specific heat capacities in cal. x g⁻¹ × (°degree C)⁻¹ of the solvent and cyanuric chloride respectively, whereupon in a given case within at most 3 minutes after bringing the cyanuric chloride and solvent into contact the flowing mixture is cooled to the desired storage temperature.

14 Claims, 1 Drawing Figure

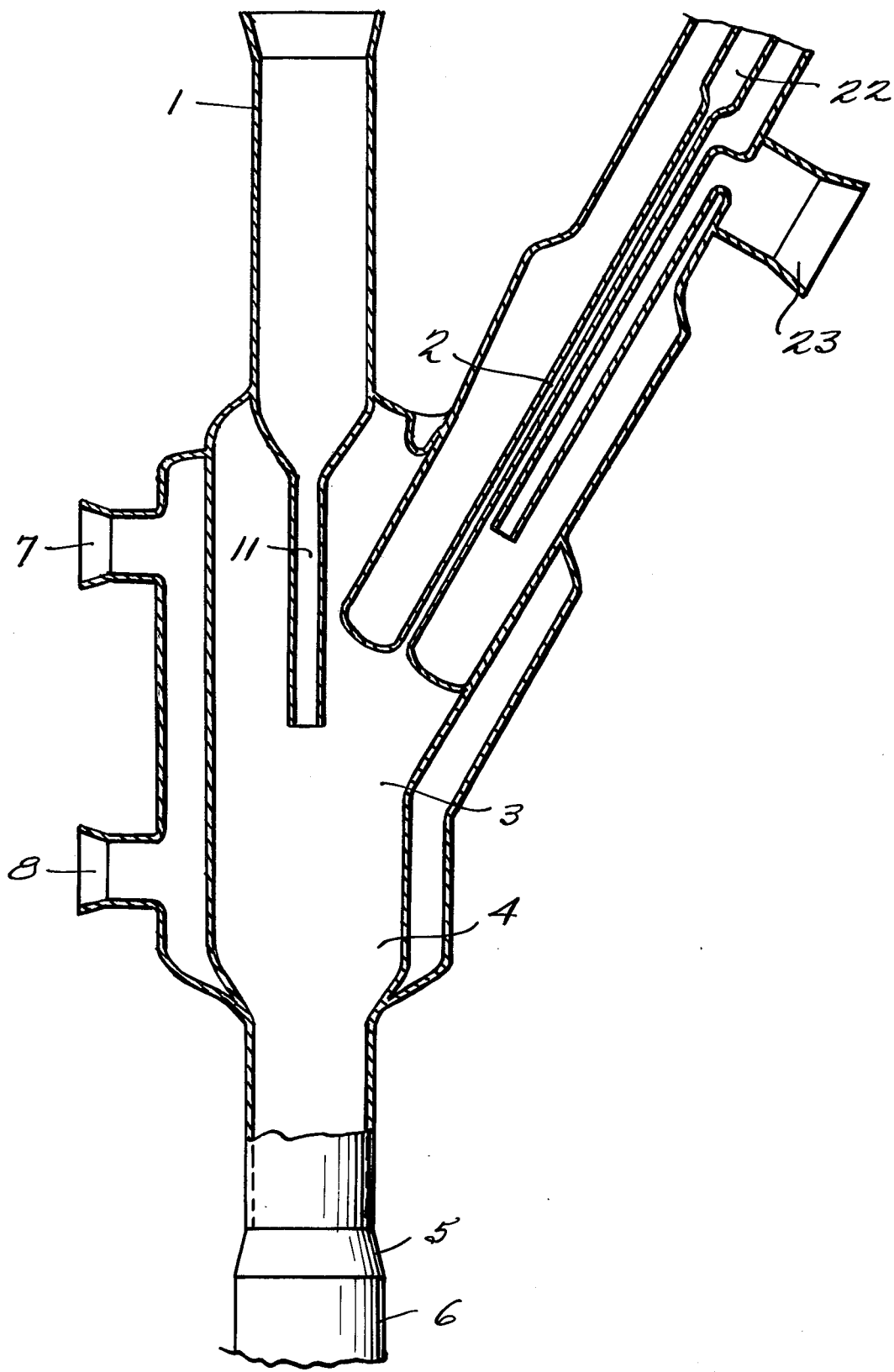

PROCESS FOR THE PRODUCTION OF SOLUTIONS OR SUSPENSIONS OF CYANURIC CHLORIDE IN AQUEOUS ORGANIC SOLVENTS

It is known that cyanuric chloride can be relatively easily reacted with nucleophilic reagents. Under suitable reaction conditions, these reactions under certain circumstances can even take place stepwise, i.e., by successive replacement of one, two, or all three chlorine atoms of the cyanuric chloride, see Ullmanns Enzyclopacordie der Technischen Chemie (1954), Vol. 5, page 23. These reaction possibilities are the basis for many highly important industrial syntheses of interesting cyanuric chloride derivatives useful as herbicides, vulcanization aids, etc.

For most reactions of this type, however, it is necessary that the cyanuric chloride be added in a reactive form, i.e, in solution or suspension, see Molls, German Offenlegungsschrift 1,545,840. In addition, there are known a number of processes in which cyanuric chloride in solid form is added in an organic solvent, see Tandon, German Auslegeschrift No. 1,964,619, and related U.S. Pat. No. 3,883,515, or in water, see German Offenlegungsschrift No. 1,545,840, or in strongly cooled organic-aqueous systems, see German Offenlegungsschrift No. 1,695,117 whereupon the cyanuric chloride solutions or suspensions obtained are reacted as soon as possible after their production.

As quick as possible reaction or further working up of the cyanuric chloride solutions or suspensions to stable products is therefore necessary because cyanuric chloride as the acid chloride of cyanuric acid especially in solution or suspension exhibits considerable reactivity and, for example, as all acid chlorides, is hydrolyzed by water. Thereby with the splitting off of hydrochloric acid there is finally formed cyanuric acid.

From the known very high reaction enthalpy of the reaction of cyanuric chloride with water to form cyanuric acid, there can be measured with what violence that kind of hydrolysis reaction can run, in part up to explosion.

Because of the very low solubility of cyanuric chloride in water (see Ullmann 1954 loc. cit.), however, suspensions of cyanuric chloride can be produced. For this purpose there is introduced molten or liquid cyanuric chloride into water. Although cyanuric chloride has a melting point of about 146°C., there occurs negligible hydrolysis in the contact of the hot cyanuric chloride with water, see Wojahn, German Offenlegungsschrift No. 1.670,731 and related Wojahn, U.S. Pat. No. 3,575,880. This is in contrast to soluble acid chlorides, which, when they are contacted hot with water are known to react even explosively, see Wojahn, German Offenlegungsschrift 1,670,731 and Wojahn U.S. Pat. No. 3,575,880.

Of course, if cyanuric chloride is not dissolved or suspended in pure aqueous systems but in organic-aqueous systems in which it has considerable solubility there is observed a substantially quicker hydrolysis. Therefore, it is necessary to handle solutions or suspensions in organic-aqueous systems as much as possible only at low temperatures, whereby cyanuric chloride naturally cannot be added as a liquid. Only in this manner can the speed of hydrolysis be kept relatively low.

Especially in the presence of protic solvents, as for example acetone-water systems, there have been measured enormously high hydrolysis speeds even at 10°C. (see Rys et al, Helv. Chem. Acta. Vol. 54, 1 No. 14 (1971), pages 163–176).

On a stoichiometrical basis, however, relatively small water contents in organic solvents are sufficient to permit a hydrolysis of cyanuric chloride dissolved or suspended in such systems. For example, an about 2.6% content of water in acetone is sufficient to hydrolyze completely a 10% solution of cyanuric chloride in acetone.

Although in organic-aqueous systems the molar water concentration is naturally smaller than in systems predominantly aqueous in character, the speed of hydrolysis is comparatively large, namely, through the presence of the so-called "insulated" water molecules in organic-aqueous systems in contrast to the water molecules aggregated to tetrahedrons in pure water (see K. Schwabe, Elektrometrische pH —Messungen unter extremen Bedingungen, Verl. Chemie (1960) pages 72 and seq. and P. Salomaa, Acta Chemica Scand., Vol. 11 (1957), pages 125–131.

However, organic-aqueous systems are of especial industrial interest for the production of cyanuric chloride solutions or suspensions, since they permit industrial, i.e., always more or less water containing solvents to be used. Also, the expense of recycling with this type of solvent can be kept low, if the cyanuric chloride solutions or suspensions. are employed in subsequent processes.

As is already described in Wojahn, German Offenlegungsschrift 1,670,731 and Wojahn, U.S. Pat. No. 3,575,880, it is of especial industrial advantage that cyanuric chloride not be brought into the solvent or suspension agent in solid, difficultly handleable form, but instead be added directly in the form of the melt. Of special industrial value were aqueous-organic systems in which cyanuric chloride are dissolved or suspended coming out of the liquid form.

However, such types of systems until the present time are not producible without thereby always hydrolyzing a considerable portion of the cyanuric chloride introduced, in applicants' experience even more than 50% and in some cases up to 100%.

The purpose of the invention is to produce organic aqueous solutions or suspensions of cyanuric chloride without mentionable hydrolysis taking place.

It has now been found that these kinds of solutions or suspensions of liquid cyanuric chloride can be produced if both the liquid cyanuric chloride and the organic-aqueous so event are mixed together while being agitated, the liquid cyanuric chloride at a temperature between its melting point and 200°C. is led into the flowing organic-aqueous solvent with a velocity of Vcy (in kg per hour) wherein $$V_{cy} = \frac{P - P_{LM}}{100 - P} \times V_{LM}$$

where

P is the desired concentration of cyanuric chloride in the solution or suspension to be produced in weight %,
$P_{LM}$ [in weight %] is the concentration of cyanuric chloride in the solvent used which also includes O,
$V_{LM}$ is the velocity of the solvent added in kg/h, and
$P_{LM}$, $V_{LM}$ and $T_{LM}$, the temperature of the added solvent, are so selected that the expression $$T_x = \frac{T_{LM} + \frac{V_{Cy}}{V_{LM}} \times \frac{C_p(Cy)}{C_p(LM)} \times T_{Cy}}{1 + \frac{V_{Cy}}{V_{LM}} \times \frac{C_p(Cy)}{C_p(LM)}}$$

does not exceed the boiling temperature in ° C. of the solvent used and wherein $C_p(LM)$ and $C_p(Cy)$ signify the specific heat capacities in cal. $\times g^{-1} \times (°\text{degree C})^{-1}$ of the solvent and cyanuric chloride respectively, whereupon in a given case within at most three minutes after bringing the cyanuric chloride and solvent into contact the flowing mixture is cooled to the desired storage temperature.

Preferably $T_X$ has the value 50, or even more preferably 40. The boiling temperature of the solvent is based on the pressure which occurs at the place of mixing the cyanuric chloride and solvent. Generally, $T_X$ has a value of 0° C to boiling point of the solvent (expressed in ° C).

The cyanuric chloride and solvent can be introduced to each other in either laminar or turbulent flow. However, turbulent flow is preferred.

There can be employed all kinds of mixing apparatus which permit the realization of the above named flow velocity ratios, especially mixing nozzles, preferably such as that described immediately below.

An arrangement, which resembles a water-jet pump, consists of a so-called nozzle mixing space in which the solvent jet enters from a vertical so-called main nozzle, while the liquid cyanuric chloride is sprayed in from a laterally arranged side nozzle heated up to the top.

The exit opening for the mixture of cyanuric chloride and solvent formed at the lower end of the nozzle mixing space as well as the subsequent falling distance of the mixture inside the apparatus must be so measured that the pressure under which the existing liquid column stands is maintained in such equilibrium to the prevailing pressure in the nozzle mixing space that the heated side nozzle is not wetted by the liquid surface in the nozzle mixing space.

If the apparatus is operated under normal pressure the weight of the existing fluid column is held in equilibrium exactly to the lower pressure produced at the main nozzle by the flow of the solvent. Correspondingly, the falling distance must be adjusted to the exit opening.

The invention will be understood best in connection with the drawings wherein the single FIGURE illustrates the nozzle employed.

Referring more specifically to the drawings a main nozzle 1 leads into a nozzle mixing space 3 which has a turbulence zone 4 and an exit opening 5.

The end of the neck 11 of the nozzle 1 lies below the lowest point of the side nozzle 2. The numeral 22 designates the nozzle stem, 23, 7 and 8 are the inlet or outlet openings for the heating liquid.

The complete falling space 6 is not shown.

The boiling temperature $T_{sdp}$ of the solvent should not exceed 120° C. if possible.

As organic-aqueous solvents there can used, for example, binary, ternary, or quaternary systems or systems of higher order of water and aliphatic, cycloaliphatic or aromatic hydrocarbons or halohydrocarbons which are liquid at temperatures of about 20°C. or are liquefiable under the mixing pressure, as, for example, straight or branched chain alkanes with 5 to 17 carbon atoms, e.g., pentane, isopentane, hexane, octane, isooctane, 2-ethyl hexane, decane, dodecane, heptadecane, cycloalkanes, such as cyclopentane and cyclohexane, as well as decalin, benzene, toluene, xylene (o, m or p xylene or mixtures thereof), ethyl benzene, methylene chloride, chloroform, carbon tetrachloride, mono, di, tri and tetrachloroethylene, trichloroethane, perfluoroheptane, perfluorohexane, methylene bromide, ehtylidene chloride, ethylidene bromide, chlorofluoroalkanes such as trichloro-trifluoroethane, chlorobenzene, chlorofluorobenzenes such as m-chlorobenzotrifluoride, as well as ketones such as acetone, methyl ethyl ketone, diethyl ketone, methyl isobutyl ketone, cyclohexanone, or cyclopentanone, carboxylic acid esters such as ethyl acetate, methyl acetate, methyl propionate, methyl butyrate, propyl acetate or ethyl propionate, or ethers such as diethyl ether, dipropyl ether, diisopropyl ether, methyl n-butyl ether or alcohols such as isopropyl alcohol, methyl alcohol, ethyl alcohol, butyl alcohol or isobutyl alcohol or solutions or suspensions of cyanuric chloride in the named systems ($P_{LM}$ weight %). As said, mixtures of the named materials are also usable; but it is preferred to use the halogen-compounds pure or mixed with other halogen-compounds only.

The process of the invention is preferably suitable for the production of solutions or suspensions of liquid cyanuric chloride in water containing organic solvents of the type of aromatic hydrocarbons such as benzene or toluene and/or aliphatic ketones such as acetone, methyl ethyl ketone or methyl isobutyl ketone especially, binary, single phase systems of water, acetone and toluene are suited for the process as organic-aqueous solvents for the production of cyanuric chloride solutions or suspensions of liquid cyanuric chloride.

Especially favorable results, also particularly in regard to the storage stability of the cyanuric chloride solutions or suspensions are obtained if there are used ternary systems of toluene, acetone and water, preferably those with more than 50 weight % toluene. Thus, there are included in such preferred ternary systems 65 to 75% toluene, 34.8 to 75% acetone and 0,2 to 10% water.

The water content of the organic-aqueous solvents used is of minor significance. Generally, there are used organic-aqueous solvent system with less than 50 weight % water, preferably those with less than 10 weight % water, especially those with 5 weight % or less of water. The amount of water can be as little as weight % of the solvent system.

If the mixture of cyanuric chloride and organic-aqueous solvent obtained according to the invention is not to be immediately further processed, it must be promptly cooled, i.e., generally there is up to 3 minutes time to reach the temperature through cooling at which the hydrolysis of cyanuric chloride in solutions or suspensions proceeds tolerably slowly. Namely, in reference to the same concentrations of cyanuric chloride as are kept in solutions or suspensions according to conventional processes with powdery cyanuric chloride and the same organic solvents with the same water contents.

For this cooling, there basically must be considered two possibilities: (a) Subsequent cooling by heat exchangers. (b) Subsequent cooling by partial evaporation of the volatile components of the solvents used.

Preferably method (b) is carried out in such a manner that the mixture of cyanuric chloride and solvent formed in the apparatus is drawn off into an evacuated receiver in which there is evaporated a portion of the solvent. Thereby, there occurs in this receiver a quick cooling through the evaporation of the solvent or the heat of vaporization necessary therefor.

Then the cooled cyanuric chloride solution or suspension can be continuously pumped out of the receiver, in a given case over a level regulator.

The temperature to which the cyanuric chloride solution or suspension must be cooled by evaporation of solvent or by a subsequently provided heat exchanger depends on how the cyanuric chloride solution or suspension is to be further used or how high is the water or cyanuric chloride content in this solution or suspension.

For example, it is sufficient to only cool to 25° C. an 18 weight % cyanuric chloride solution which is produced from liquid cyanuric chloride and acetone containing 5 weight % of water, if this cyanuric chloride solution is required to have for the subsequent operating process a degree of hydrolysis up to 0.5% and is to be used within 10 minutes after its production.

On the contrary, if there is produced a 9 weight % cyanuric chloride solution from liquid cyanuric chloride with acetone containing 20 weight % of water in order to not exceed the degree of hydrolysis of 0.5% the solution must be cooled to 5° C. and this solution likewise be used in 10 minutes.

On the contrary, if this latter solution is worked up not earlier but after 20 minutes, then the solution must be cooled to -10° C.

The necessary cooling capacity, which it is understood depends on the desired end temperature, is easily ascertained from the heat of evaporation of the solvent, the amount of solution or suspension present and the heat capacity of the mixture if this cooling capacity results from evaporative cooling.

The above-named degree of hydrolysis indicates how many moles of cyanuric acid in the hypothetical case, i.e., if the hydrolysis immediately goes to cyanuric acid, can be formed per 100 moles of cyanuric chloride. The hydrolysis to intermediate products, namely to monochlorodihydroxy-s-triazine or to dichlorohydroxy-s-triazine is according to this definition considered as corresponding to the equivalent molar amount of cyanuric acid. Generally, in this kind of organic-aqueous solvent system the hydrolysis to such intermediate products in contrast to the formation of cyanuric acid is of minor significance.

The degree of hydrolysis was ascertained in the following manner:

By the degree of hydrolysis of the cyanuric chloride is meant how many moles of HCl per 100/3 = 33.3 moles of cyanuric chloride in the solution or suspension are formed by hydrolysis. Therefore, the degree of hydrolysis is determined by titration of the HCl formed according to the following method: 10 ml of a sample fo the cyanuric chloride solution or suspension being investigated was pipetted into a 100 ml measuring cylinder and filled up with pure acetone. From the thus obtained solution, 5 ml were pipeted into 50 ml of dioxane and titrated in this solution with 0.05 molar, aqueous Hg(II) acetate solution against diphenylcarbazone.

The calculation of the degree of hydrolysis (according to the above-given definition) results from the following relation:

$$\% \text{ hydrolysis} = 122.8 \times \frac{\text{ml-Hg acetate}}{\rho \times \%\text{Cy}}$$

whereby $\rho$ stands for the density in grams per cm$^3$ and % Cy stands for the percent content (weight %) of cyanuric chloride of the solution or suspension being tested.

In continuous recovery of the named solutions or suspensions, liquid cyanuric chloride is fed in a jet of the water containing organic solvent which already contains dissolved or suspended cyanuric chloride through carrying out the recycling. In this case $P_{LM}$, i.e., the concentration of the solvent added to cyanuric chloride is not equal to zero.

By suitable selection of the proportion of the circulating solution or suspension and of the solution or suspension removed from the cycle or the corresponding freshly added solvent to the cycle, as well as at relatively low cyanuric chloride feeding velocities (Vcy is very small) there can be produced a relatively high cyanuric chloride concentration in the circulating solution or the solution removed from the cycle. Of course, it is then assumed that the residence time in the cycle up to discharge from the cycle as well as the subsequent handling up to further use or cooling is less than 3 minutes, at best less than 30 seconds, or less than 10 seconds. By installing suitable coolers in the cycle in this case the heat brought in by the liquid cyanuric chloride can be drawn off entirely or partially.

Unless otherwise indicated all parts and percentages are by weight.

The process can comprise, consist essentially of or consist of the steps set forth and the composition can comprise, consist essentially of or consist of the materials set forth.

One suitable solvent mixture is water containing industrial acetone. Another suitable solvent mixture is a mixture of 29.1% by weight acetone, 70 weight % toluene and 0.9 weight % water.

COMPARATIVE EXAMPLE NO. 1

2 liters of technical acetone containing 0.2% per weight of water and having a temperature of 20° C were stirred in a 4-liter glass round-bottomed flask. Into the acetone 184 ml of liquid (i.e., molten) cyanuric-chloride of 160° C had been poured within 10 minutes. By the cyanuric-chloride-addition the temperature of the mixture raised to about 30° C while turning to be turbid showing the precipitation of cyanuric acid. An analysis of the mixture 10 minutes after the end of the cyanuric-chloride-addition showed a degree of hydrolysis of 3,5%.

COMPARATIVE EXAMPLE NO. 2

2 liters of technical acetone containing 5% per weight of water and having a temperature of 20° C were stirred in a 4 liter glass-round-bottomed flask. To the flask was fitted a reflux-condenser — the whole equipment was protected against air-humidity by a calcium-chloride-tube. Into the acetone 184 ml of liquid cyanuric-chloride of 160° C were poured within 10 minutes. By the addition of the cyanuric-chloride, the temperature of the mixture raised first to about 30°C — within the next 10 minutes it increased by internal heat evolving (reaction-healt, especially heat of hydrolysis) until strong refluxing was to be observed. In spite of intensive cooling by a cooling-bath within about 10 minutes after the end of the cyanuric-chloride-addition practically the whole cyanuric-chloride was hydrolyzed to give cyanuric-acid. (Degree of hydrolysis measured by analysis: 98%).

The experiment had been repeated under the same conditions except the "pouring-in-time": Instead of pouring the 184 ml of liquid cyanuric-chloride into the acetone within 10 minutes this operation had been done with 25 minutes. Result: At the end of the cyanuric-chloride-addition the hydroysis-reaction led to an explosion.

EXAMPLE 1

Into a "recycling-system" containing 1068 ml of circulating technical acetone, the water content of which had been 0,2 % per weight, liquid cyanuric-chloride of a temperature of 160° C was injected by a mixing-nozzle. During the cyanuric-chloride-injection, the acetone-jet was held at a speed of 284 kg acetone per hour. The cyanuric-chloride-injection speed was 4,2 kg per hour. Over all, 90, 5 ml liquid cyanuric-chloride were added to get a 14, 5% per weight solution of cyanuric-chloride in the (water containing) acetone circulating in the cycle. After the addition of the cyanuric-chloride-quantity mentioned above, a partial stream of this cyanuric-chloride-solution was taken continuously out of the cycle while fresh acetone and liquid cyanuric-chloride were injected continuously in the same ratio as contained in the solution and the cycle. The cyanuric-chloride-solution was taken out of the cycle at a rate of 567 ml per minute corresponding to an average resting time of the mixture (i.e., the solution) in the cycle of about 2,8 minutes. The cyanuric-chloride-solution collected in this way was completely clear and showed even after a 10 minutes-storage at 25°C (solution-temperature!) a degree of hydrolysis of not more than 0,2%; 90 hours later — stored at 25° C —the degree of hydrolysis was 2%.

EXAMPLE 2

Using the same equipment as described in example 1 and using a similar processing a 14,5% per weight cyanuric-chloride-solution in acetone containing 0,2 % of water was prepared. In contrast to the processing of the experiment of example 1, the cyanuric-chloride-solution taken out of the cycle had been expanded into a 4-liter-round-bottomed flask, which had been evacuated by a vacuum-pump connected with an automatic pressure-control to a constant pressure of 60 torr (i.e., 80 mbar). Therefore — corresponding to the dependence of the vapor-pressure of acetone from its temperature-acetone distilled off out of the cyanuric-chloride-solution-collecting-flask. As a consequence, the cyauric-chloride-acetone-mixture was concentrated and cooled simultanously. After 30 minutes of continuous run of the equipment, the mixture in the collecting-flask showed a stationary temperature of 0°C — it was a 19,8% per weight suspension of cyanuric-chloride in acetone, showing a degree of hydrolysis (measured 10 minutes after coming out of the cycle) of not more than 0.1%. After allowing the temperature to raise to about 15°C (i.e., the temperature of saturation of a 19, 8% solution of cyanuric-chloride in acetone), this suspension turned to be a completely clear solution — even after storage for 18 hours at 25° C; when the analysis-result showed a degree of hydrolysis of only 0,7%.

EXAMPLE 3

For the injection of the liquid cyanuric-chloride into technical acetone containing 5% per weight of water a special glass-mixing-nozzle had been used: The technical acetone jet streamed out of the main nozzle, a tube of 5 millimeters diameter and had a speed of 285 kg acetone per hour. The cyanuric-chloride-injection was realized by a second nozzle which was heated by a heating liquid up to its outlet. The liquid cyanuric-chloride had a temperature of 180° C and was injected as a jet of 50,3 kg per hour speed.

The mixture-jet leaving the nozzle-mixing-chamber was collected in an evacuated receiver, the pressure in it was controlled by an automatic system connected with a vacuum pump and held constantly at 80 torr (0,107 bar). Out of this receiver, acetone was distilled continously because of the low pressure in connection with the temperature of the mixture — thus the mixture contained in the receiver was cooled by the heat of vaporization of the acetone distilling off. The acetone distilling had been condensed in an attached cooler and was collected. By this procedure, a stationary temperature of 15° C had been reached in the receiver. By an automatic level control the level in the receiver had been held constant while cyanuric-chloride-solution was removed from the receiver by a pump, pumping into a stirred storage-tank. Summarizing, in this way there had been produced 280 kg per hour of an approximately 18% per weight solution of cyanuric-chloride in technical acetone, collected in the storage-tank at a temperature of 15° C. Analysis results: 10 minutes after production a degree of hydrolysis of 0, 5% had been found; after 30 minutes storage, the degree of hydrolysis was 1, 5%, after 2,5 hours 4, 4% and after 22 hours at 15° C it was 17, 4%.

EXAMPLE 4

Using a glass-nozzle with 5 millimeters diameter, there had been produced an acetone-jet (20° C), technical acetone with a water-content of 20% per weight). The jet had a speed of approx. 150 kg per hour. Into this jet liquid cyanuric-chloride of 160 ° C had been injected at a rate of approx. 13 kg per hour using a second nozzle which was heated up to its outlet by a heating liquid. The resulting mixture-jet had been collected in a receiver attached to the nozzle-equipment. The pressure in this receiver had been held at 50 torr (0,07 bar) by a vaccum-pump in connection with an automatic pressure-control. The receiver was connected with a subsequent condenser and a separate collecting-tank for receiving the solvent distilled off. By a separate pump controlled by an automatic level-controller situated at the receiver the cyanuric-chloride-solvent-mixture cooled by evaporation had been withdrawn at a rate of 150 kg per hour and pumped into a storage-tank By this way an approx. 9% per weight cyanuric-chloride-solution in technical acetone was produced. This solution showed a temperature of 5° C.

Analysis result: Degree of hydrolysis after production 0, 5%; 30 minutes later 1, 5%; 1 hour after production 12% and 10 hours after production 50% (Storage at 5° C).

EXAMPLE 5

Using a glass-nozzle with 5 millimeters diameter, there had been produced an acetone-jet (15 ° C; technical acetone with a water-content of 2% per weight). The jet had a speed of approx. 280 kg per hour. Into this jet liquid cyanuric-chloride of 190° C had been injected at a rate of 93 kg per hour using a second nozzle which was heated up to its outlet by a heating-liquid. The resulting mixture-jet had been collected in a receiver attached to the nozzle-equipment. The pressure in this receiver had been held at 70 torr (0,09 bar) by a vacuum-pump in connection with an automatic pressure-control. The receiver was connected with a subsequent condenser and a separate collecting-tank for receiving the solvent distilled off. By a separate pump controlled by an automatic level-controller situated at the receiver the cyanuric-chloride-solvent-mixture cooled by evaporation had been withdrawn at a rate of 300 kg per hour and pumped into a storage-tank.

By this way an approx. 31% per weight cyanuric-chloride-suspension in technical acetone was produced. This suspension showed a temperature of 10° C.

Analysis result: Degree of hydrolysis 10 minutes after production 0, 25%; 4 hours after production 2,4%; 20 hours after production 4, 0% (storage at 10° C).

EXAMPLE 6

Using a glass-nozzle with 5 millimeters diameter, there had been produced an acetone-jet (25° C; technical acetone with a water-content of 1% per weight). The jet had a speed of approx. 290 kg per hour. Into this jet liquid cyanuric-chloride of 160° C had been injected at a rate of 118,4 kg per hour using a second nozzle which was heated up to its outlet by a heating-liquid. The resulting mixture-jet had been collected in a receiver attached to the nozzle-equipment. The pressure in this receiver had been held at 30 torr (0,04 bar) by a vacuum-pump in connection with an automatic pressure-control. The receiver was connected with a subsequent condenser and a separate collecting-tank for receiving the solvent distilled off. By a separate pump controlled by an automatic level-controller situated at the receiver the cyanuric-chloride-solvent-mixture cooled by evaporation had been withdrawn at a rate of 275 kg per hour and pumped into a storage-tank.

By this way an approx. 43% per weight cyanuric-chloride-suspension in technical acetone was produced. This suspension showed a temperature of 0° C.

Analysis result: Degree of hydrolysis 5 minutes after production 0, 3%; 1 hour after production 0, 8%; 10 hours after production 0, 9% (storage at 0° C).

EXAMPLE 7

Using a glass-nozzle with 5 millimeters diameter, there had been produced a solvent-jet (20 ° C; solvent = a mixture consisting of 70% toluene, 29, 1% acetone and 0, 9% water; all percentages given in weight — %). The jet had a speed of approx. 270 kg per hour. Into this jet liquid cyanuric-chloride of 170° C had been injected at a rate of 110 kg per hour using a second nozzle which was heated up to its outlet by a heating-liquid. The resulting mixture-jet had been collected in a receiver attached to the nozzle-equipment. The pressure in this receiver had been held at 40 torr (0,05 bar) by a vacuum-pump in connection with an automatic pressure-control. The receiver was connected with a subsequent condenser and a separate collecting-tank for receiving the solvent distilled off. By a separate pump controlled by an automatic level-controller situated at the receiver the cyanuric-chloride-solvent-mixture cooled by evaporation had been withdrawn at a rate of 300 kg per hour and pumped into a storage-tank.

By this way an approx. 30% per weight cyanuric-chloride-suspension in technical acetone was produced. This suspension showed a temperature of 5° C.

Analysis result: Degree of hydrolysis 15 minutes after production 0, 1%; 1 hour after production less than 0, 1% 16 hours after production 0, 24% (storage at 5° C).

After further storage at 22 ° C for 24 hours the degree of hydrolysis was not greater than 0, 56%. Dilution of this suspension with acetone gave a completely clear solution.

What is claimed is:

1. A process for the production of a solution or suspension of cyanuric chloride in a water containing organic solvent comprising mixing liquid cyanuric chloride and the organic-aqueous solvent while they are agitated, said process including leading the liquid 200°chloride at a temperature between its melting point and 200° C. into the flowing organic-aqueous solvent, the cyanuric chloride having a velocity Vcy in kg/hr where $$V_{cy} = \frac{P - P_{LM}}{100 - P} \times V_{LM}$$

where

P is the desired concentration of cyanuric chloride in said solution or suspension, $P_{LM}$ is the concentration of cyanuric chloride in the solvent, $V_{LM}$ $V_{LM}$ is the velocity of the added solvent in kg/h, and $P_{LM}$, $V_{LM}$, the temperature of the added solvent are so selected that the equation $$T_x = \frac{T_{LM} + \frac{V_{cy}}{V_{LM}} \times \frac{C_p(Cy)}{C_p(LM)} \times T_{cy}}{1 + \frac{V_{cy}}{V_{LM}} \times \frac{C_p(Cy)}{C_p(LM)}}$$

does not exceed the boiling point in ° C. of the solvent and wherein $C_P(LM)$ and $C_P(Cy)$ indicate the specific heat capacities in cal. $\times$g $^{-}\times$ degree $C^{-1}$ of the solvent and cyanuric chloride respectively.

2. The process of claim 1 including the further step of cooling the flowing mixture to the desired storage or use temperature within three minutes.

3. The process of claim 2 wherein $P_{LM}$ is 0.

4. The process of claim 2 wherein $P_{LM}$ is greater than 0

5. The process of claim 1 wherein $T_X$ is 40 to 50.

6. The process of claim 1 wherein $T_X$ is 50.

7. The process of claim 1 wherein $T_X$ is 40.

8. The process of claim 1 wherein the water containing solvent consists essentially of aqueous acetone.

9. The process of claim 1 wherein the solvent boils at a temperature not over 120° C.

10. The process of claim 1 wherein the amount of water is less than 50% of the total solvent.

11. The process of claim 10 wherein the amount of water is less than 10% of the total solvent.

12. The process of claim 11 wherein the amount of water is less than 5% of the total solvent.

13. The process of claim 12 wherein the solvent has a boiling point not over 120° C. and $T_X$ is 40–50.

14. The process of claim 1 wherein the solvent is an aqueous mixture consisting essentially of 29.1% acetone, 70% toluene and 0.9% water.

* * * * *